US012612400B2

(12) United States Patent
Kim et al.

(10) Patent No.: US 12,612,400 B2
(45) Date of Patent: Apr. 28, 2026

(54) PYRROLOPYRIDINE DERIVATIVE PREPARATION METHOD

(71) Applicant: ST PHARM CO., LTD., Gyeonggi-do (KR)

(72) Inventors: Kyungjin Kim, Seoul (KR); Uk-Il Kim, Gyeonggi-do (KR); Hyung Tae Bang, Gyeonggi-do (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 387 days.

(21) Appl. No.: 18/271,534

(22) PCT Filed: Jan. 11, 2021

(86) PCT No.: PCT/KR2021/000301
§ 371 (c)(1),
(2) Date: Jul. 10, 2023

(87) PCT Pub. No.: WO2022/149638
PCT Pub. Date: Jul. 14, 2022

(65) Prior Publication Data

US 2024/0317737 A1 Sep. 26, 2024

(51) Int. Cl.
*C07D 471/04* (2006.01)
*C07D 403/06* (2006.01)

(52) U.S. Cl.
CPC ......... *C07D 471/04* (2013.01); *C07D 403/06* (2013.01)

(58) Field of Classification Search
CPC .. C07D 471/04; C07D 403/06; A61K 31/437; A61P 31/12
See application file for complete search history.

(56) References Cited

U.S. PATENT DOCUMENTS

| | | | |
|---|---|---|---|
| 2010/0179139 A1 | 7/2010 | Bamborough | |
| 2014/0249162 A1 | 9/2014 | Son et al. | |

FOREIGN PATENT DOCUMENTS

| | | |
|---|---|---|
| EP | 2781519 A1 | 9/2014 |
| EP | 4201405 | 6/2023 |
| JP | 2014522858 | 9/2014 |
| KR | 20130054211 | 5/2013 |
| KR | 20150141275 | 12/2015 |
| KR | 10-2015-0141275 | 2/2016 |
| KR | 20190141152 | 12/2019 |
| KR | 10-2019-0141152 | 8/2020 |
| WO | WO 2005/103003 | 11/2005 |
| WO | WO 2012/102985 | 8/2012 |
| WO | WO 2013/012649 | 1/2013 |
| WO | WO 2013/012649 A1 | 1/2013 |
| WO | WO 2018/174320 A1 | 9/2018 |
| WO | WO 2022/039551 | 2/2022 |

OTHER PUBLICATIONS

Supplementary European Search Report issued for European Application No. 21917801.9, dated Aug. 23, 2024, 11 pages.
Estevez et al., "Multicomponent reactions for the synthesis of pyrroles," *Chemical Society Reviews*, vol. 39, No. 11, p. 4402, Jan. 1, 2010.
Office Action for Japanese Patent Application No. 2023-512003, dated Feb. 6, 2024, 8 pages (w/English translation).
Uchida et al., "Preparation and Characterization of (5-Methyl-2-oxo-1,3-dioxol-4-yl) methyl Thiamine Sulfides," *The Pharmaceutical Society of Japan*, 126(3), 179, 2006. (w/English Abstract).
Office Action for Russian Application No. 2023105729, dated Oct. 11, 2023, with English Translation.
Christ et al., "Rational design of small-molecule inhibitors of the LEDGF/p75-integrase interaction and HIV replication," *Nature Chemical Biology*, vol. 6, pp. 442-448, May 16, 2010.
International Search Report and Written Opinion issued for International Application No. PCT/KR2021/011116 on Dec. 1, 2021.
Office Action for Brazilian Application No. BR112023003144-3, dated Feb. 25, 2025, with English-language machine translation.
Zanatta et al., "Convenient One-Pot Synthesis of N-Substituted 3-Trifluoroacetyl Pyrroles," *Synlett* 5:755-758, 2009.
ISR and Written Opinion from International Application No. PCT/KR2021/000301, issued on Oct. 1, 2021.

*Primary Examiner* — Clinton A Brooks
*Assistant Examiner* — Kyle Nottingham
(74) *Attorney, Agent, or Firm* — Klarquist Sparkman, LLP

(57) ABSTRACT

The present invention relates to a method for preparing a pyrrolopyridine derivative compound exhibiting antiviral activity, and a novel intermediate used therein. The preparation method of the present invention enables reaction steps to be reduced through effective process development and a high purity pyrrolopyridine derivative compound to be prepared in a high yield, and thus enables production costs to be remarkably reduced so as to be economical and to be suitable for mass production.

13 Claims, No Drawings

PYRROLOPYRIDINE DERIVATIVE PREPARATION METHOD

CROSS REFERENCE TO RELATED APPLICATION

This is the U.S. National Stage of International Application No. PCT/KR2021/000301, filed Jan. 11, 2021, which is incorporated herein by reference in its entirety.

TECHNICAL FIELD

The present invention relates to a method for preparing a pyrrolopyridine derivative exhibiting antiviral activity.

BACKGROUND ART

Acquired Immunodeficiency Syndrome (AIDS) is caused by infection with human immunodeficiency virus (HIV). For the treatment of AIDS, enzyme inhibitors have been developed according to HIV's mechanism of action. According to the mode of action, the enzyme inhibitors are classified into a nucleoside reverse transcriptase inhibitor (NRTI), a protease inhibitor (PI), a fusion inhibitor, and an integrase inhibitor. Since the reverse transcriptase inhibitor, protease inhibitor, and fusion inhibitor have problems such as side effects, drug interactions, drug resistance and so on, thus development of integrase inhibitors is actively progressing.

Integrase inhibitors are divided into catalytic site inhibitors and non-catalytic site inhibitors depending on mechanisms thereof. A representative example of the catalytic site integrase inhibitor is Raltegravir. The mechanism of the non-catalytic site integrase inhibition was introduced by Zeger Debyser et al. (Frauke Christ, Zeger Debyser at al., Nature Chemical Biology, 2010, Vol. 6, 442), and no drug regarding this has been successfully developed.

However, Raltegravir, a catalytic site integrase inhibitor, was also found to exhibit drug resistance. In the case of HIV, if the medication discontinuation occurs, the medication taken is no longer effective since the latent HIV is reactivated and drug resistance develops, and thus the development of non-catalytic site integrase inhibitors is being attempted as a medication capable of solving the development of drug resistance. In particular, a pyrrolopyridine derivative represented by the following Chemical Formula I is known as the non-catalytic site integrase inhibitor:

[Chemical Formula I]

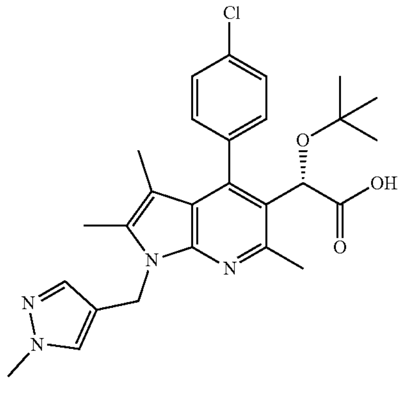

International Publication WO 2013/073875 does not disclose the compound of Chemical Formula I in a direct manner, but discloses a method for preparing derivatives encompassing the compound of Chemical Formula I. However, since numerous steps (a total of 16 steps) are required to obtain derivatives similar to the compound of Chemical Formula I, the preparation method above is not suitable for mass production.

In addition, International Publication WO 2018/174320 directly discloses a compound of Chemical Formula I and a method for preparing the same. However, since the preparation method thereof was performed as it is according to the preparation method disclosed in International Publication Patent WO 2013/073875 and all steps required column purification, the preparation method is not suitable for mass production.

Therefore, it is necessary to develop a novel preparation method capable of preparing the pyrrolopyridine derivative compound of Chemical Formula I in high yield and high purity by improving the above inefficient preparation method.

DISCLOSURE

Technical Problem

An object of the present invention is to provide a method for preparing a pyrrolopyridine derivative capable of preparing a pyrrolopyridine derivative with high purity and high yield, thereby lowering the production cost and achieving efficient process steps to be suitable for mass production.

In addition, another object of the present invention is to provide a novel intermediate used in the preparation method above.

Technical Solution

In one general aspect, the present invention provides a method for preparing a pyrrolopyridine derivative represented by the following Chemical Formula I:

[Chemical Formula I]

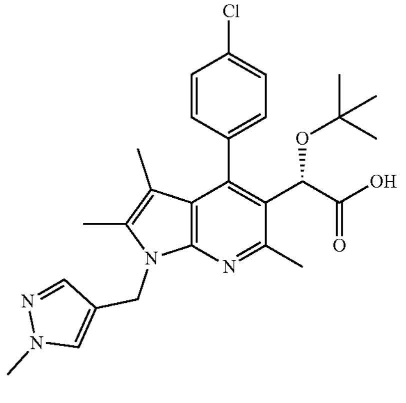

Specifically, the preparation method of the present invention may comprise the following steps (S-1) to (S-5):

(S-1) a first step of preparing a compound represented by the following Chemical Formula 3 by cyclization of a compound represented by the following Chemical Formula 1 or a salt thereof and a butanone derivative represented by the following Chemical Formula 2;

(S-2) a second step of preparing a compound represented by the following Chemical Formula 4 by cyclization of the compound represented by Chemical Formula 3 and an acetopyruvate derivative;

(S-3) a third step of preparing a compound represented by the following Chemical Formula 5 from the compound represented by Chemical Formula 4 by a chiral reduction;

(S-4) a fourth step of preparing a compound represented by the following Chemical Formula 6 from the compound represented by Chemical Formula 5 by an alkylation; and (S-5) a fifth step of preparing a compound represented by the following Chemical Formula I from the compound represented by Chemical Formula 6 by a hydrolysis:

[Chemical Formula 1]

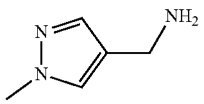

[Chemical Formula 2]

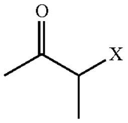

[Chemical Formula 3]

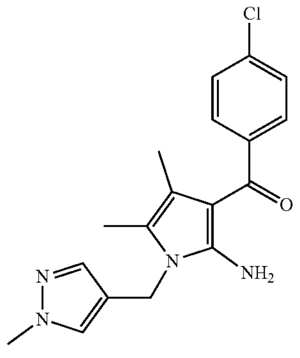

[Chemical Formula 4]

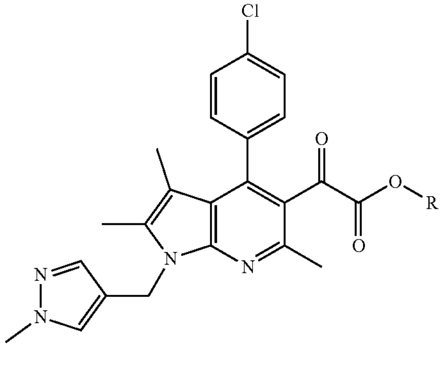

-continued

[Chemical Formula 5]

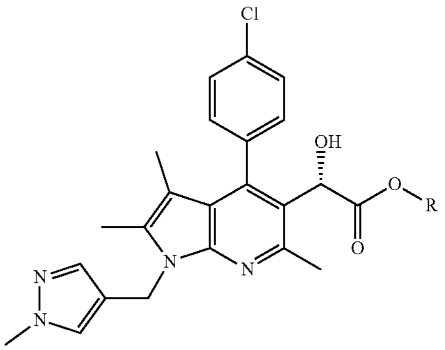

[Chemical Formula 6]

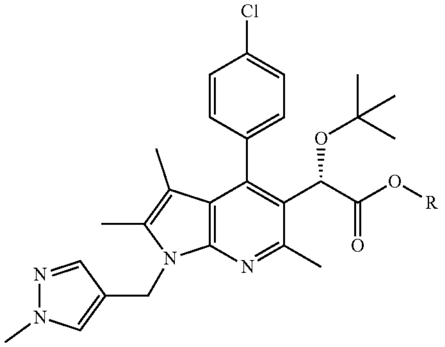

[Chemical Formula I]

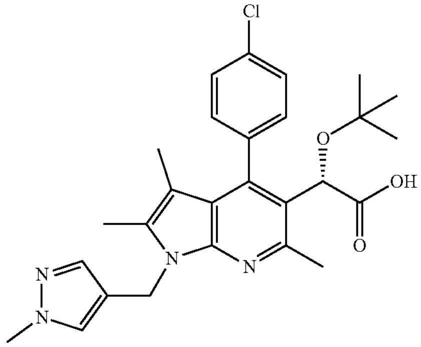

in the Chemical Formula above, X is Cl, Br or I, and R is $C_{1-4}$alkyl.

According to preparation methods disclosed in International Publication WO 2013/073875 and International Publication WO 2018/174320, the compound represented by Chemical Formula I above was subjected to a total of 16 steps, which was not suitable for mass production. However, the preparation method of the present invention enables the compound represented by Chemical Formula I to be prepared only through a total of 5 steps (S-1) to (S-5), which is able to be applied to mass production.

In addition, all of the compounds represented by Chemical Formulas 3 to 6 prepared in steps (S-1) to (S-4) are useful intermediates for preparing the pyrrolopyridine derivative compound represented by Chemical Formula I.

Hereinafter, each of the steps (S-1) to (S-5) is separately described.

Step (S-1)

In the present invention, the step (S-1) is to prepare the pyrrole ring derivative compound represented by Chemical Formula 3 by cyclization of the pyrazole derivative compound represented by Chemical Formula 1 or a salt thereof and the butanone derivative represented by Chemical Formula 2 (Reaction Scheme 1):

[Reaction Scheme 1]

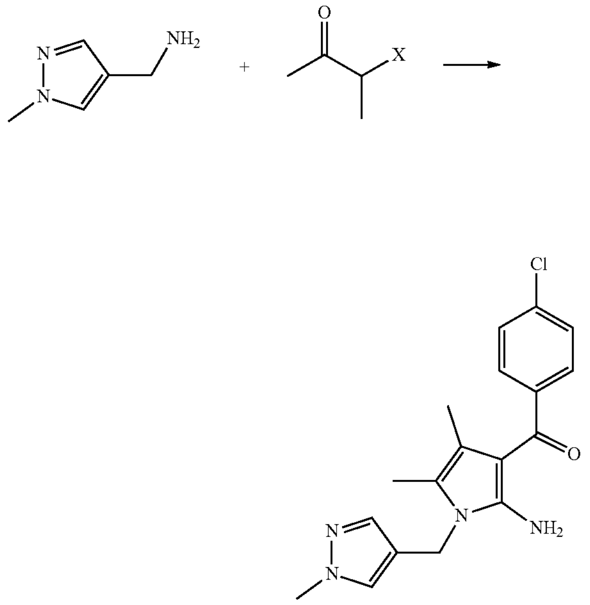

in the Reaction Scheme above, X is Cl, Br or I, and R is $C_{1-4}$alkyl.

According to an embodiment of the present invention, the reaction may be performed by a cyclization of (1-methyl-1H-pyrazol-4-yl)methanamine hydrochloride together with a butanone derivative (ex. 3-chlorobutan-2-one) and 4-chlorobenzoylacetonitrile compound.

In the above reaction, an organic solvent commonly used in the cyclization may be used. For example, the solvent may be methanol, ethanol, isopropyl alcohol, tert-butanol, tetrahydrofuran, 1,4-dioxane, acetone, or a mixture thereof. Specifically, ethanol may be used, but is not limited thereto.

In addition, the reaction may be performed at 30 to 60° C., more specifically at 35 to 45° C., but is not limited thereto.

After the reaction, one or more steps of separating or purifying the product may be additionally performed, but is not limited thereto. For example, in an example of the present invention, a product with high purity was obtained by stirring the product of the reaction in an organic solvent, toluene.

Step (S-2)

In the present invention, the step (S-2) is to prepare the pyrrolopyridine derivative compound represented by Chemical Formula 4 by cyclization using the pyrrole derivative compound represented by Chemical Formula 3 as a starting material (Reaction Scheme 2):

[Reaction Scheme 2]

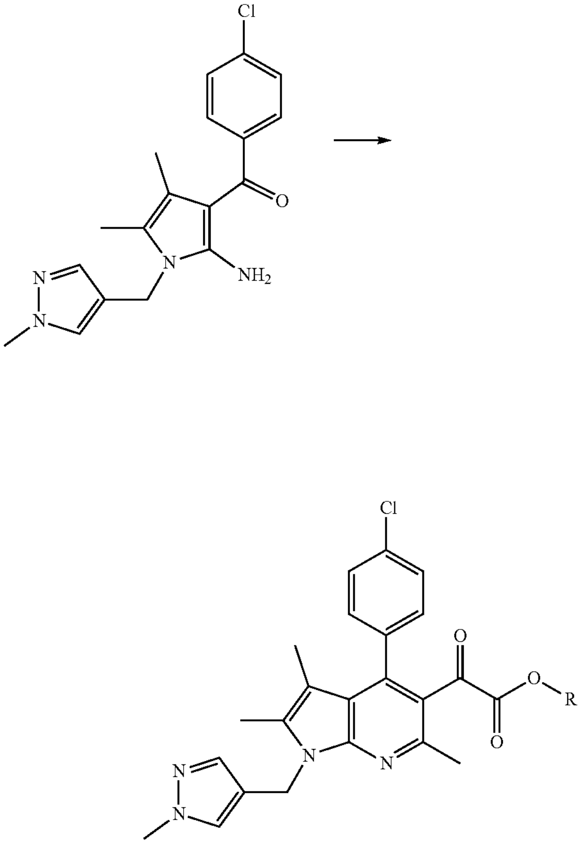

in the Reaction Scheme above, R is $C_{1-4}$alkyl.

According to an embodiment of the present invention, in the reaction, the compound represented by Chemical Formula 4 may be prepared by reaction with ethyl acetopyruvate. Here, R is ethyl.

The acid used in the reaction may be hydrochloric acid, acetyl chloride, sulfuric acid, p-toluenesulfonic acid, methanesulfonic acid, or a mixture thereof. Specifically, hydrochloric acid may be used, but is not limited thereto.

Further, in the above reaction, an organic solvent commonly used in the cyclization reaction may be used. Here, as the organic solvent, ethanol, 1,4-dioxane, acetonitrile, dimethyl sulfoxide, dimethylformamide, dimethylacetamide, or a mixture thereof may be used. Specifically, acetonitrile may be used, but is not limited thereto.

In addition, the reaction may be performed at 40 to 80° C., more specifically at 60 to 65° C., but is not limited thereto.

Step (S-3)

In the present invention, the step (S-3) is to prepare the pyrrolopyridine derivative compound having a chiral alcohol structure represented by Chemical Formula 5 by reducing a ketone group of the pyrrolopyridine derivative compound represented by Chemical Formula 4 through a chiral reduction (Reaction Scheme 3):

[Reaction Scheme 3]

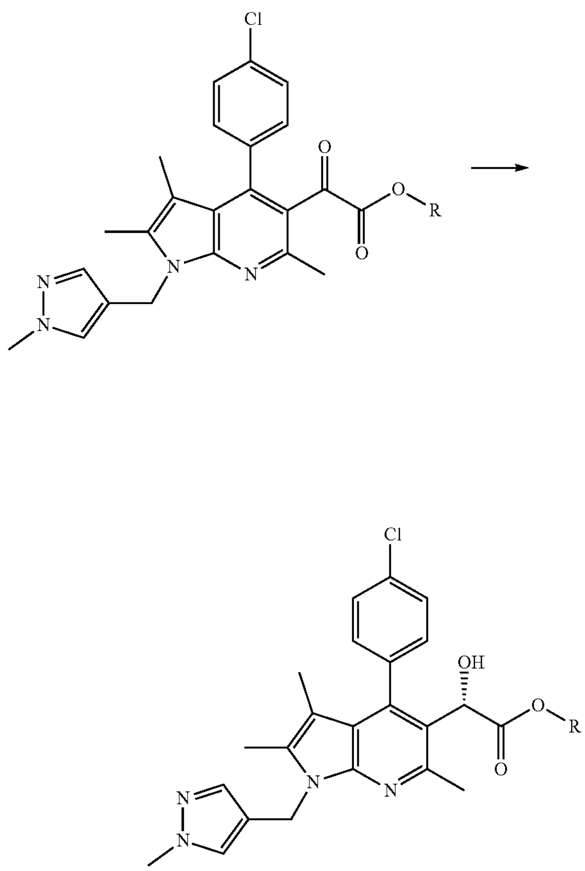

in the Reaction Scheme above, R is $C_{1-4}$alkyl.

According to an embodiment of the present invention, the chiral reduction may be performed using a combination of (R)-(+)-2-methyl-CBS-oxazaborolidine and catecholborane.

Further, according to another embodiment of the present invention, the chiral reduction may be performed using a combination of (pentamethylcyclopentadienyl)rhodium(III) dichloride dimer and (1S,2S)-N-(p-toluenesulfonyl)-1,2-diphenylethanediamine.

In the above reaction, an organic solvent commonly used in the chiral reduction may be used. For example, the organic solvent may be toluene, acetonitrile, or a mixture thereof, but is not limited thereto.

In addition, the reaction may be performed at −10 to 10° C., more specifically at −5 to 5° C., but is not limited thereto.

Step (S-4)

In the present invention, the step (S-4) is to prepare the pyrrolopyridine derivative compound represented by Chemical Formula 6 by the alkylation of a chiral alcohol in the pyrrolopyridine derivative compound represented by Chemical Formula 5 (Reaction Scheme 4):

[Reaction Scheme 4]

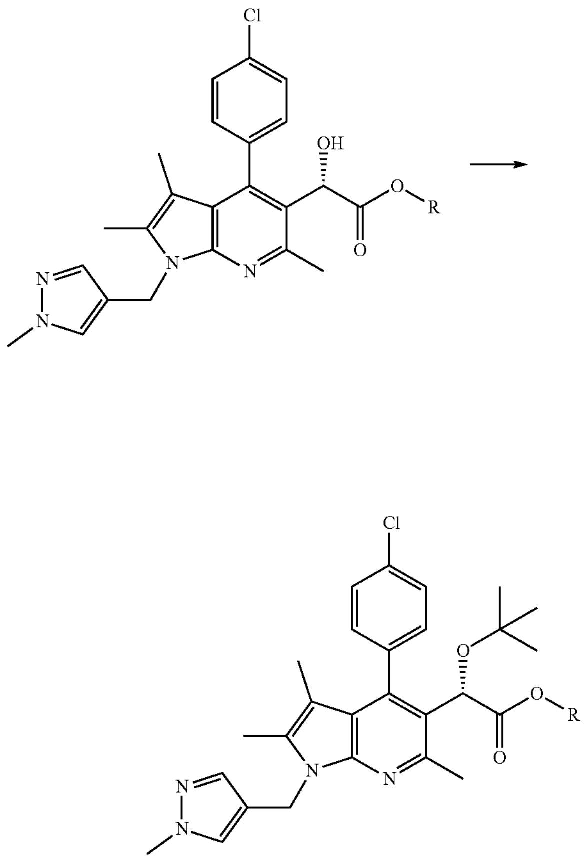

in the Reaction Scheme above, R is $C_{1-4}$alkyl.

According to an embodiment of the present invention, the alkylation may be performed using tert-butyl acetate. Here, the reaction may be performed under perchloric acid, but is not limited thereto.

According to another embodiment of the present invention, the alkylation may be performed using isobutene.

Here, the reaction may be performed under perchloric acid also, but is not limited thereto.

In the above reaction, an organic solvent commonly used in the alkylation may be used. For example, as the organic solvent, a halogenated solution may be used, and in particular, a dichloromethane solution may be used. However, examples of the organic solvent are not limited thereto.

In addition, the reaction may be performed at −5 to 30° C., more specifically at −5 to 20° C., but is not limited thereto.

Step (S-5)

In the present invention, the step (S-5) is to prepare the carboxylic acid compound represented by Chemical Formula I by the hydrolysis of the ester compound represented by Chemical Formula 6 (Reaction Scheme 5):

[Reaction Scheme 5]

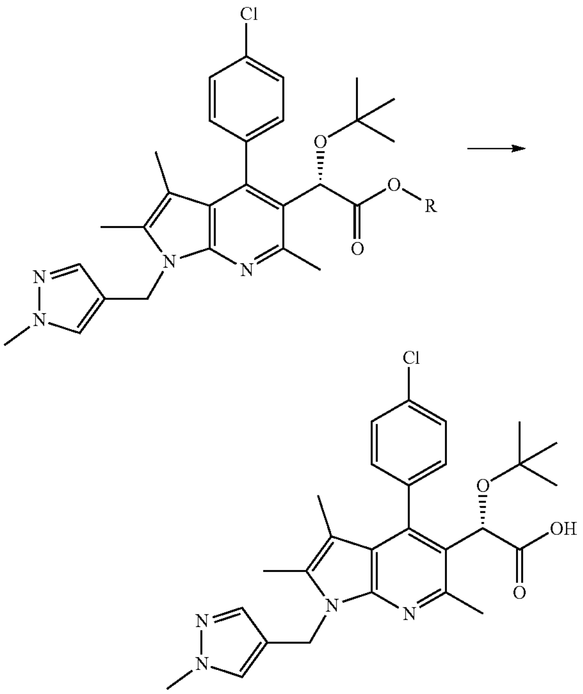

in the Reaction Scheme above, R is $C_{1-4}$alkyl.

According to an embodiment of the present invention, the hydrolysis may be a basic hydrolysis. The base used in the reaction may be lithium hydroxide, sodium hydroxide or potassium hydroxide, and may be specifically sodium hydroxide. However, examples of the base are not limited thereto.

In the above reaction, an organic solvent commonly used in the hydrolysis may be used. Here, as the organic solvent, tetrahydrofuran, methanol, ethanol, isopropyl alcohol, a water solution, or a mixture thereof may be used. Specifically, a mixture of tetrahydrofuran and methanol may be used, but is not limited thereto.

In addition, the reaction may be performed at 20 to 80° C., more specifically at 40 to 50° C., but is not limited thereto.

Advantageous Effects

The preparation method of the present invention may reduce reaction steps through efficient process development to prepare pyrrolopyridine derivative compound with a high purity and high yield, thereby greatly reducing the production cost to be economical, which is suitable for mass production.

BEST MODE

Hereinafter, preferred examples are provided to aid understanding of the present invention. However, the following Examples are only provided to more easily understand the present invention, but the content of the present invention is not limited by these Examples.

Examples

In Examples of the present invention, a pyrrolopyridine derivative compound represented by Chemical Formula I was prepared according to Reaction Scheme I below:

[Reaction Scheme I]

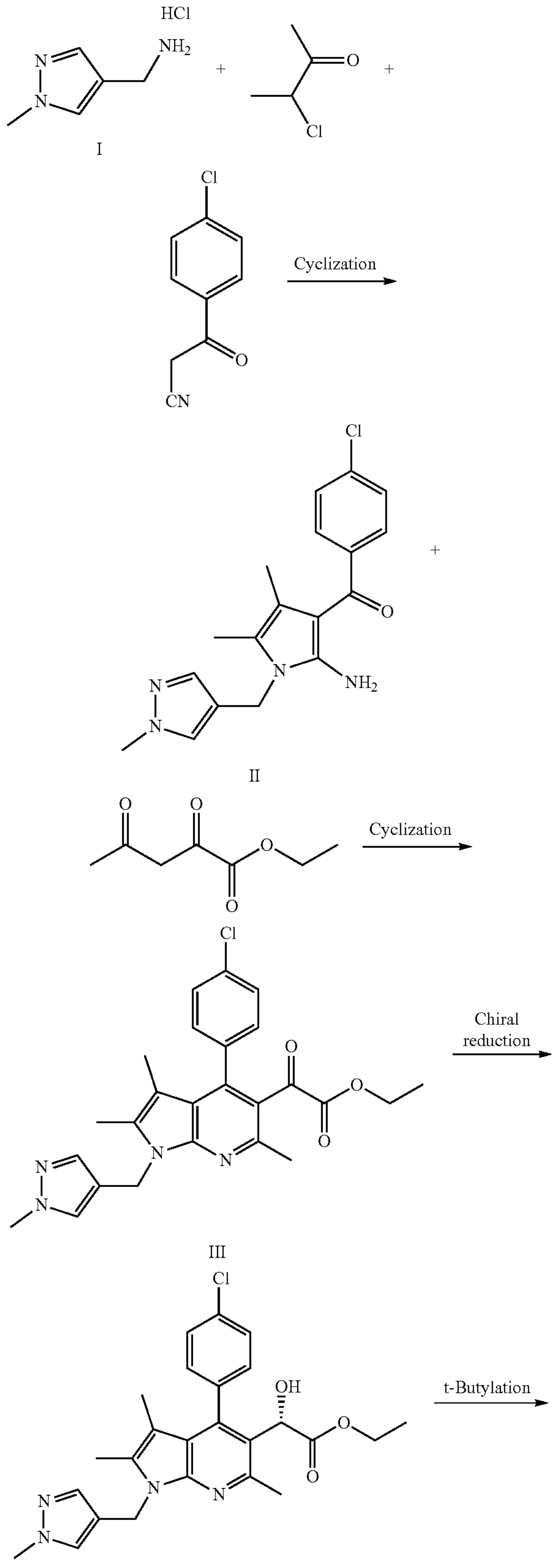

I

II

III

IV

-continued

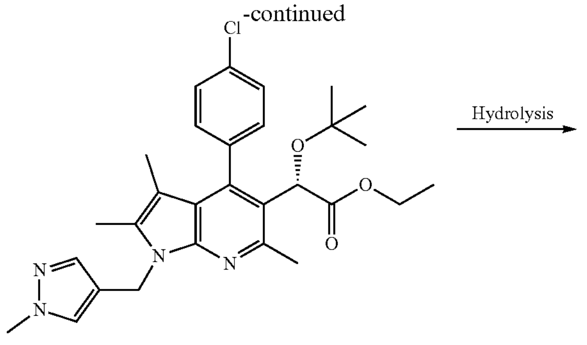

V

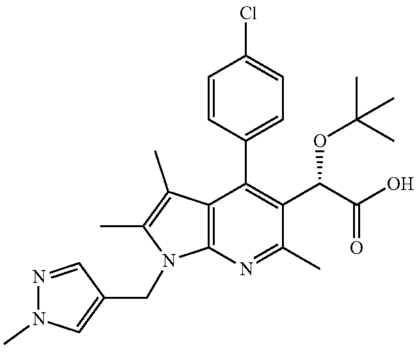

VI

Example 1: Preparation of (2-amino-4,5-dimethyl-1-((1-methyl-1H-pyrazol-4-yl)methyl)-1H-pyrrol-3-yl) (4-chlorophenyl)methanone

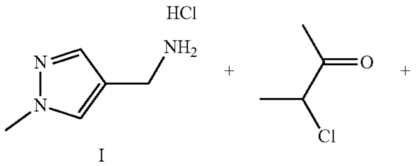

I

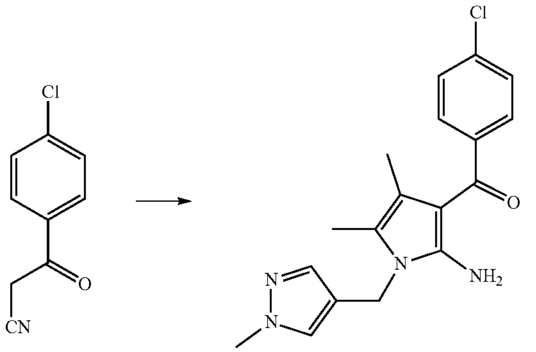

II (1-Methyl-1H-pyrazol-4-yl)methanamine hydrochloride (10 g, 67.76 mmol) was diluted in 135 mL of ethanol, then diisopropylethylamine (29.5 mL, 169.37 mmol) and 4-chlorobenzoylacetonitrile (13.38 g, 74.52 mmol) were added, and the reaction solution was stirred while raising the temperature to 35 to 40° C. 3-chlorobutan-2-one (10.3 mL 101.62 mmol) was slowly added dropwise over 30 minutes, and the mixture was stirred for 3 hours while maintaining the temperature at 35 to 40° C. After the reaction was completed, the mixture was cooled to 10° C., and 400 mL of water was added dropwise thereto, followed by stirring for 30 minutes. The precipitated crystals were filtered, and the resulting solid was diluted with 200 mL of toluene, followed by stirring at 40° C. for 30 minutes. The mixture was slowly cooled to 15° C. and stirred for 30 minutes, then filtered and dried under reduced pressure to afford the desired product (17.98 g, 77%).

$^1$H-NMR 400 Hz (DMSO-$d_6$): 7.58 (s, 1H), 7.45-7.43 (m, 2H), 7.35-7.33 (m, 3H), 7.18 (s, 2H), 4.80 (s, 2H), 3.78 (s, 3H), 1.99 (s, 3H), 1.36 (s, 3H);

LCMS: m/z 343.1 [M+1].

Example 2: Preparation of ethyl 2-(4-(4-chlorophenyl)-2,3,6-trimethyl-1-((1-methyl-1H-pyrazol-4-yl)methyl)-1H-pyrrolo[2,3-b]pyridin-5-yl)-2-oxoacetate

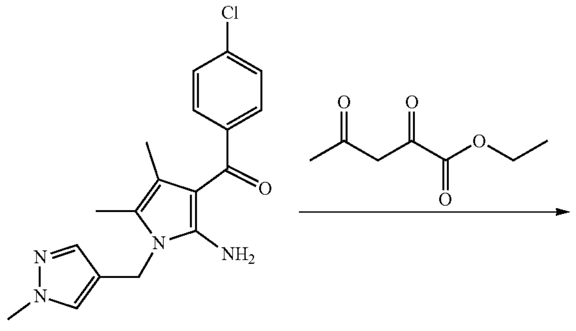

II

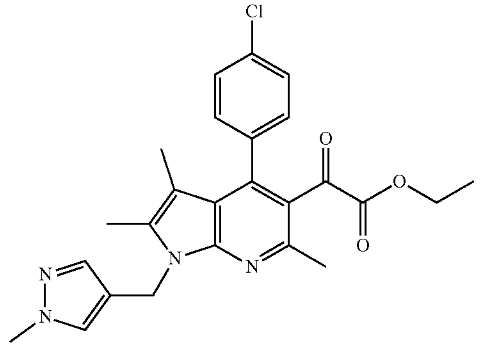

III (2-Amino-4,5-dimethyl-1-((1-methyl-1H-pyrazol-4-yl)methyl)-1H-pyrrol-3-yl) (4-chlorophenyl)methanone (17.6 g, 51.34 mmol) prepared in the Example 1 was diluted in 103 mL of acetonitrile, and then ethyl acetopyruvate (10.81 mL, 77.00 mmol) was added under nitrogen. While stirring the reaction solution, a 4M-hydrochloric acid dioxane solution (38.5 mL, 154.01 mmol) was added dropwise thereto, followed by stirring at 62 to 65° C. for 20 hours or more, and completion of the reaction was confirmed by HPLC. The reaction solution was concentrated, and diluted with 528 mL of ethyl acetate and 352 mL of saturated sodium hydrogen carbonate aqueous solution at 0° C., followed by stirring for 10 minutes, and the organic layer was extracted at room temperature. The separated organic layer was washed twice with 352 mL of saturated sodium hydrogen carbonate aqueous solution, dehydrated with anhydrous sodium sulfate, filtered, and concentrated under reduced pressure. The resulting residue was purified by silica gel column chromatography (ethyl acetate:hexane=1:1) to afford the desired product (10.2 g, 42.7%).

$^1$H-NMR 400 Hz ($CDCl_3$): 7.43-7.37 (m, 3H), 7.26-7.22 (m, 3H), 5.34 (s, 2H), 3.86-3.83 (m, 5H), 2.69 (s, 3H), 2.32 (s, 3H), 1.63 (s, 3H), 1.12 (t, J=7.2 Hz, 3H);

LCMS: m/z 465.1 [M+1].

Example 3-1: Preparation of ethyl (S)-2-(4-(4-chlorophenyl)-2,3,6-trimethyl-1-((1-methyl-1H-pyrazol-4-yl)methyl)-1H-pyrrolo[2,3-b]pyridin-5-yl)-2-hydroxyacetate

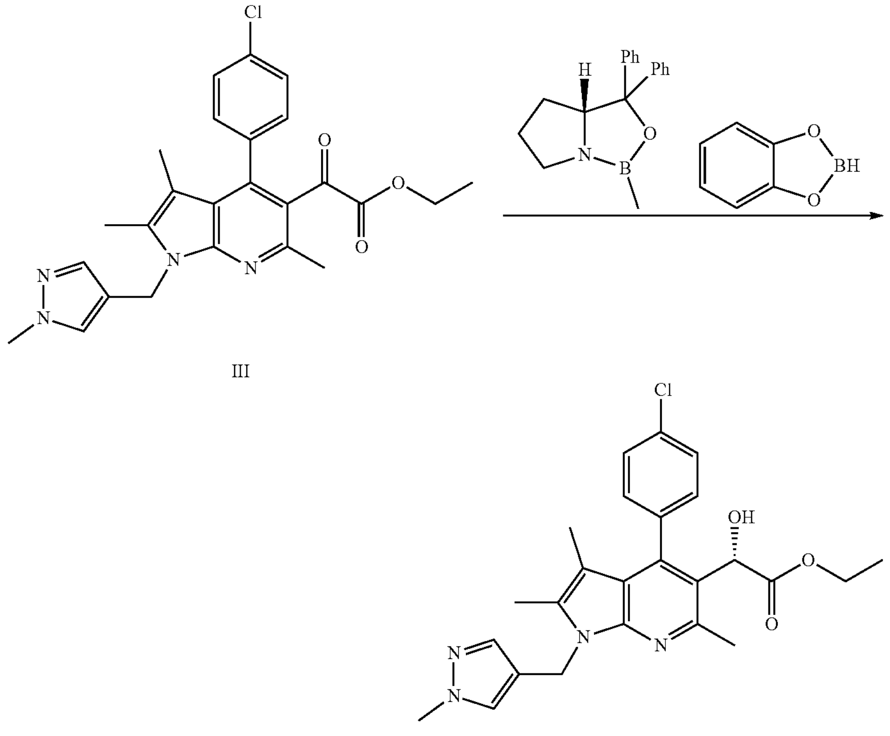

III

IV

Ethyl 2-(4-(4-chlorophenyl)-2,3,6-trimethyl-1-((1-methyl-1H-pyrazol-4-yl)methyl)-1H-pyrrolo[2,3-b]pyridin-5-yl)-2-oxoacetate (6.67 g, 14.35 mmol) prepared in the Example 2 was diluted in 48 mL of toluene, and then (R)-(+)-2-methyl-CBS-oxazaborolidine (1M toluene solution, 5.74 mL, 5.74 mmol) was added under nitrogen. The reaction mixture was cooled to −50° C., then catecholborane (1M tetrahydrofuran solution, 43.04 mL, 43.04 mmol) was slowly added dropwise over 25 minutes, and stirred at −10 to −5° C. for 8 hours. After the reaction was completed, 267 mL of heptane was added dropwise and stirred. The formed solid was stirred for 10 minutes and then filtered. The obtained solid was dissolved in 100 mL of methanol, stirred for 15 minutes, and concentrated. The concentrated residue was dissolved in 200 mL of ethyl acetate and cooled to 5 to 10° C., and 66 mL of sodium carbonate aqueous solution was added dropwise, followed by stirring for 30 minutes. The separated aqueous layer was extracted with 176 mL of ethyl acetate. The organic layer was dehydrated with anhydrous sodium sulfate, filtered, and concentrated under reduced pressure. The obtained residue was purified by silica gel column chromatography to afford the desired product (2.2 g, 32.8%, ee: 97%).

$^1$H-NMR 400 Hz (DMSO-$d_6$): 7.55-7.52 (m, 3H), 7.33-7.28 (m, 3H), 5.70 (d, J=3.6 Hz, 1H), 5.31-5.18 (m, 2H), 4.98 (d, J=3.6 Hz, 1H), 4.08-3.97 (m, 2H), 3.74 (s, 3H), 2.56 (s, 3H), 2.29 (s, 3H), 1.42 (s, 3H), 1.10 (t, J=6.8 Hz, 3H);

LCMS: m/z 467.1 [M+1].

Example 3-2: Preparation of ethyl (S)-2-(4-(4-chlorophenyl)-2,3,6-trimethyl-1-((1-methyl-1H-pyrazol-4-yl)methyl)-1H-pyrrolo[2,3-b]pyridin-5-yl)-2-hydroxyacetate (IV)

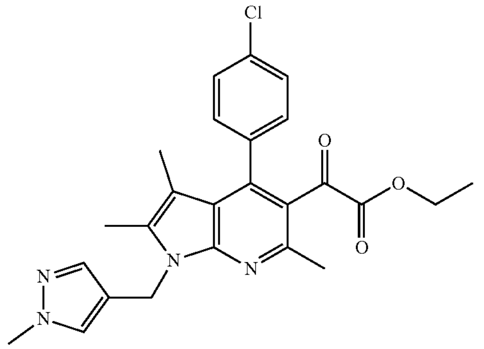

III

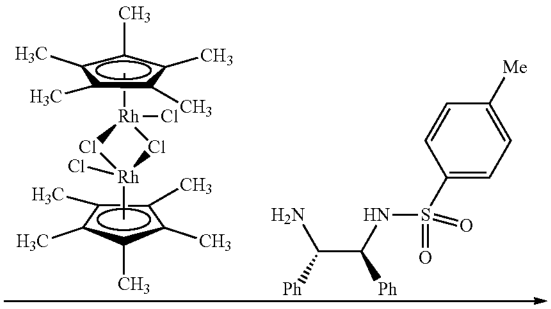

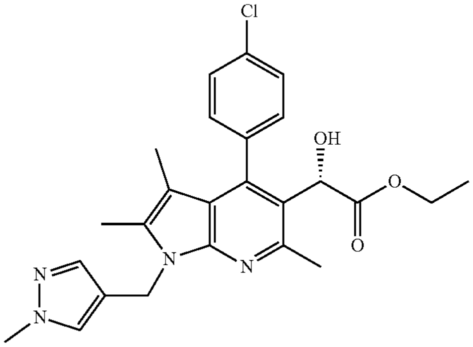

IV

Ethyl 2-(4-(4-chlorophenyl)-2,3,6-trimethyl-1-((1-methyl-1H-pyrazol-4-yl)methyl)-1H-pyrrolo[2,3-b]pyridin-5-yl)-2-oxoacetate (11.71 g, 25.19 mmol) prepared in the Example 2 was diluted in 84 mL of acetonitrile, and triethylamine (7.02 mL, 50.4 mmol) was added under nitrogen, followed by stirring for 10 minutes. After lowering the reaction temperature to −5° C. or less, formic acid (2.85 mL, 75.6 mmol) was slowly added dropwise.

To another reactor, (pentamethylcyclopentadienyl) rhodium(III) dichloride dimer (0.74 g, 1.2 mmol), (1S,2S)-N-(p-toluenesulfonyl)-1,2-diphenylethanediamine (1.1 g, 3.0 mmol), and 27 mL of acetonitrile were added, and stirred for about 10 minutes or more. While maintaining the internal temperature at 0 to 5° C., triethylamine (1.76 mL, 12.6 mmol) was added and stirred for 1 hour, and then added dropwise to the reaction solution. The reaction was performed for 60 hours at the internal temperature of −5 to 5° C. After the reaction was completed, 210 mL of ethyl acetate and 180 mL of purified water were added, and the organic layer was extracted and washed twice with purified water. The separated organic layer was dried over anhydrous sodium sulfate and filtered with a carbon filter, and the filtrate was concentrated under reduced pressure. The obtained residue was purified by silica gel column chromatography to afford the desired product (9.64 g, 82%, ee: 99%).

$^1$H-NMR 400 Hz (DMSO-$d_6$): 7.55-7.52 (m, 3H), 7.33-7.28 (m, 3H), 5.70 (d, J=3.6 Hz, 1H), 5.31-5.18 (m, 2H), 4.98 (d, J=3.6 Hz, 1H), 4.08-3.97 (m, 2H), 3.74 (s, 3H), 2.56 (s, 3H), 2.29 (s, 3H), 1.42 (s, 3H), 1.10 (t, J=6.8 Hz, 3H); LCMS: m/z 467.1 [M+1].

Example 4-1: Preparation of ethyl (S)-2-(tert-butoxy)-2-(4-(4-chlorophenyl)-2,3,6-trimethyl-1-((1-methyl-1H-pyrazol-4-yl)methyl)-1H-pyrrolo[2,3-b]pyridin-5-yl)acetate (V)

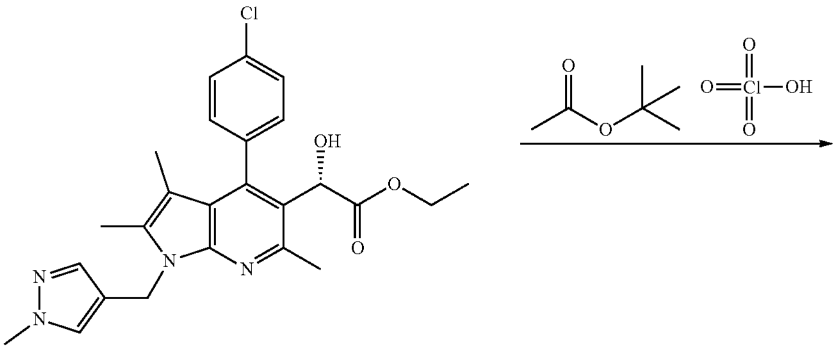

IV

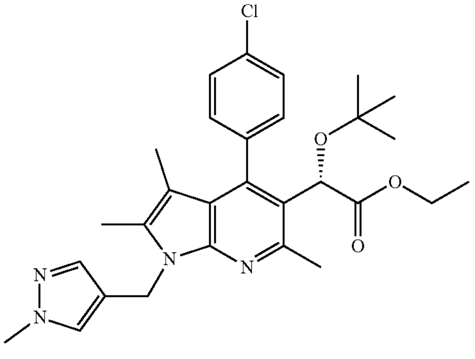

V

Ethyl (S)-2-(4-(4-chlorophenyl)-2,3,6-trimethyl-1-((1-methyl-1H-pyrazol-4-yl)methyl)-1H-pyrrolo[2,3-b]pyridin-5-yl)-2-hydroxyacetate (16 g, 34.26 mmol) prepared in the Example 3-1 was diluted in 68.5 mL of dichloromethane, and 456 mL of tert-butyl acetate was added under nitrogen. The reaction solution was cooled to 0 to 5° C., 70% perchloric acid (11.8 mL, 137.05 mmol) was slowly added dropwise over 1 hour, then the temperature was gradually raised, and stirred at 20° C. for 4 hours. The reaction solution was cooled to 0 to 5° C. and diluted with 480 mL of dichloromethane and 960 mL of saturated sodium carbonate aqueous solution, followed by stirring for 20 minutes to separate the organic layer. The separated organic layer was washed with 240 mL of water, dehydrated with anhydrous sodium sulfate, filtered, and concentrated under reduced pressure. The obtained residue was purified by silica gel column chromatography to afford the desired product (12.4 g, 69%, ee: 99%).

$^1$H-NMR 400 Hz (DMSO-$d_6$): 7.61-7.53 (m, 3H), 7.42 (dd, J=8.2 Hz, J=2 Hz, 1H), 7.34 (s, 1H), 7.30 (dd, J=8.2 Hz, J=2 Hz, 1H), 5.28-5.18 (m, 2H), 4.98 (s, 1H), 4.10-4.02 (m, 2H), 3.74 (s, 3H), 2.62 (s, 3H), 2.29 (s, 3H), 1.41 (s, 3H), 0.91 (s, 9H);

LCMS: m/z 523.2 [M+1].

Example 4-2: Preparation of ethyl (S)-2-(tert-butoxy)-2-(4-(4-chlorophenyl)-2,3,6-trimethyl-1-((1-methyl-1H-pyrazol-4-yl)methyl)-1H-pyrrolo[2,3-b]pyridin-5-yl)acetate (V)

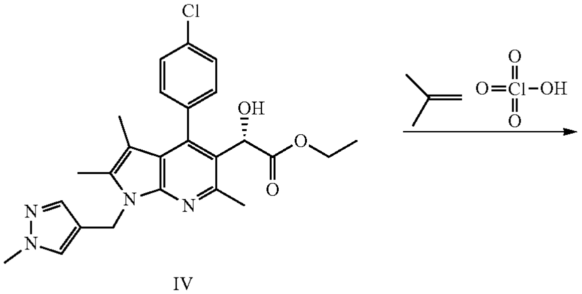

IV

-continued

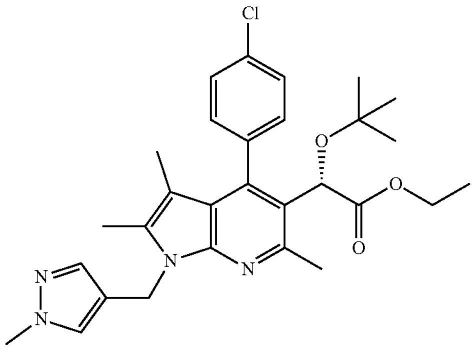

V

Ethyl (S)-2-(4-(4-chlorophenyl)-2,3,6-trimethyl-1-((1-methyl-1H-pyrazol-4-yl)methyl)-1H-pyrrolo[2,3-b]pyridin-5-yl)-2-hydroxyacetate (7 g, 14.99 mmol) prepared in the Example 3-1 was diluted in 8% isobutene dichloromethane solution (158.1 mL, 300 mmol). The reaction mixture was cooled to −5 to 0° C., and 70% perchloric acid (4.51 mL, 52.5 mmol) was added dropwise, followed by stirring at 5 to 10° C. for 24 hours. After the reaction was completed, 1N aqueous sodium hydroxide solution (55.5 mL, 57.7 mmol) was slowly added to the reaction solution at −5 to 0° C., followed by stirring at room temperature for 10 minutes. The organic layer was washed with 50 mL of water, dehydrated with anhydrous sodium sulfate, filtered, and concentrated under reduced pressure. The obtained residue was purified by silica gel column chromatography to afford the desired product (6.46 g, 82%, ee: 99%).

$^1$H-NMR 400 Hz (DMSO-$d_6$): 7.61-7.53 (m, 3H), 7.42 (dd, J=8.2 Hz, J=2 Hz, 1H), 7.34 (s, 1H), 7.30 (dd, J=8.2 Hz, J=2 Hz, 1H), 5.28-5.18 (m, 2H), 4.98 (s, 1H), 4.10-4.02 (m, 2H), 3.74 (s, 3H), 2.62 (s, 3H), 2.29 (s, 3H), 1.41 (s, 3H), 0.91 (s, 9H);

LCMS: m/z 523.2 [M+1].

Example 5: Preparation of (S)-2-(tert-butoxy)-2-(4-(4-chlorophenyl)-2,3,6-trimethyl-1-((1-methyl-1H-pyrazole-4-yl)methyl)-1H-pyrrolo[2,3-b]pyridin-5-yl)acetic acid

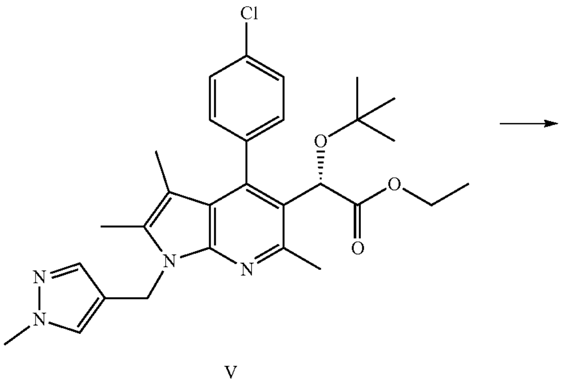

V

-continued

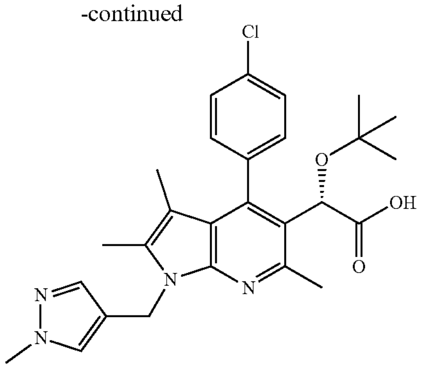

VI

Ethyl (S)-2-(tert-butoxy)-2-(4-(4-chlorophenyl)-2,3,6-trimethyl-1-((1-methyl-1H-pyrazol-4-yl)methyl)-1H-pyrrolo[2,3-b]pyridin-5-yl)acetate (13.5 g, 25.8 mmol) prepared in the Example 4-1 was diluted in 108 mL of tetrahydrofuran and 27 mL of methanol. Sodium hydroxide (3.1 g, 77.4 mmol) was added, and the mixture was stirred at 40 to 45° C. for 4 hours. After the reaction was completed, the mixture was concentrated under reduced pressure, and 120 mL of dichloromethane and 60 mL of purified water were added thereto. The mixture was cooled to 0 to 5° C., and the pH was adjusted to 4.5 to 5.0 with 2N aqueous hydrochloric acid solution. The organic layer was separated, washed with 60 mL of purified water, dehydrated with anhydrous sodium sulfate, filtered, and concentrated under reduced pressure. To the obtained residue, 30 mL of acetonitrile was added, and the mixture was stirred for 3 hours while cooling to 5 to 10° C. The precipitated crystals were filtered and dried under reduced pressure to afford the desired product (9.25 g, 72%, ee: 99%) as a white solid.

$^1$H-NMR 400 Hz (DMSO-$d_6$): 7.60 (dd, J=8.4 Hz, J=2.4 Hz, 1H), 7.56-7.53 (m, 2H), 7.46 (dd, J=8 Hz, J=2.4 Hz, 1H), 7.35 (s, 1H), 7.30 (dd, J=8.4 Hz, J=2.4 Hz, 1H), 5.28-5.19 (m, 2H), 4.93 (s, 1H), 3.74 (s, 3H), 2.63 (s, 3H), 2.29 (s, 3H), 1.42 (s, 3H), 0.89 (s, 9H);

LCMS: m/z 495.2 [M+1].

Specific parts of the present invention have been described in detail. It will be obvious to those skilled in the art that these specific descriptions are merely preferred embodiments, and the scope of the present invention is not limited thereby. Therefore, the substantial scope of the present invention will be defined by the appended claims and equivalents thereof.

The invention claimed is:

1. A method for preparing a compound represented by Chemical Formula I, the method comprising:

(S-1) a first step of preparing a compound represented by the following Chemical Formula 3 by cyclization of a compound represented by the following Chemical Formula 1 or a salt thereof and a butanone derivative represented by the following Chemical Formula 2;

(S-2) a second step of preparing a compound represented by the following Chemical Formula 4 by cyclization of the compound represented by Chemical Formula 3 and an acetopyruvate derivative;

(S-3) a third step of preparing a compound represented by the following Chemical Formula 5 from the compound represented by Chemical Formula 4 by a chiral reduction;

(S-4) a fourth step of preparing a compound represented by the following Chemical Formula 6 from the compound represented by Chemical Formula 5 by an alkylation; and (S-5) a fifth step of preparing a compound represented by the following Chemical Formula I from the compound represented by Chemical Formula 6 by a hydrolysis:

[Chemical Formula 1]

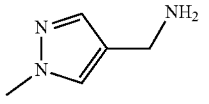

[Chemical Formula 2]

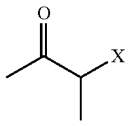

[Chemical Formula 3]

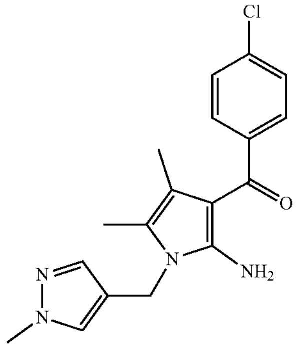

[Chemical Formula 4]

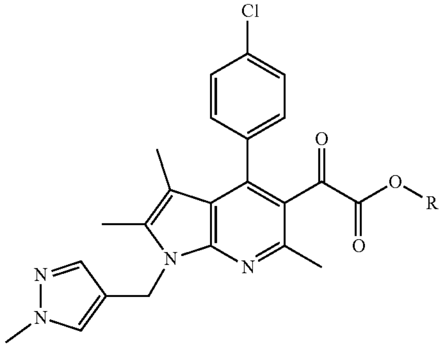

[Chemical Formula 5]

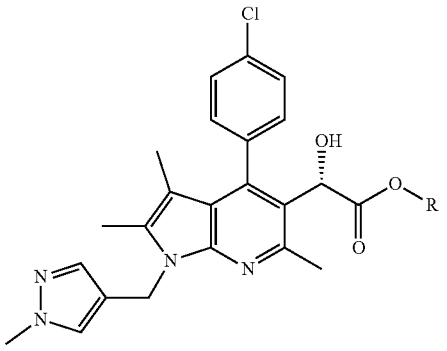

-continued

[Chemical Formula 6]

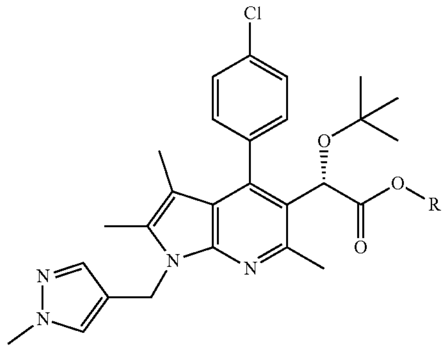

[Chemical Formula I]

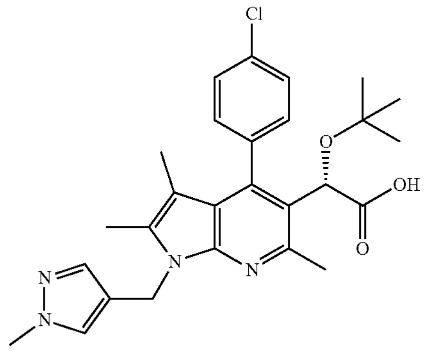

in the Chemical Formulas above,

X is Cl, Br or I, and

R is $C_{1-4}$alkyl.

2. The method of claim 1, wherein the salt of the compound represented by Chemical Formula 1 is hydrochloride.

3. The method of claim 1, wherein X is Cl.

4. The method of claim 1, wherein the step (S-1) further comprises a process of separating or purifying the precipitated compound represented by Chemical Formula 3.

5. The method of claim 1, wherein the step (S-2) is a reaction with ethyl acetopyruvate.

6. The method of claim 1, wherein the step (S-3) is a reaction with (R)-(+)-2-methyl-CBS-oxazaborolidine and catecholborane.

7. The method of claim 1, wherein the step (S-3) is a reaction with (pentamethylcyclopentadienyl) rhodium (III) dichloride dimer and (1S,2S)-N-(p-toluenesulfonyl)-1,2-diphenylethanediamine.

8. The method of claim 1, wherein the step (S-4) is a reaction with tert-butyl acetate or isobutene.

9. The method of claim 8, wherein the step (S-4) is performed under perchloric acid.

10. The method of claim 1, wherein the step (S-5) is a basic hydrolysis.

11. A compound represented by the following Chemical Formula 3 or a salt thereof:

[Chemical Formula 3]
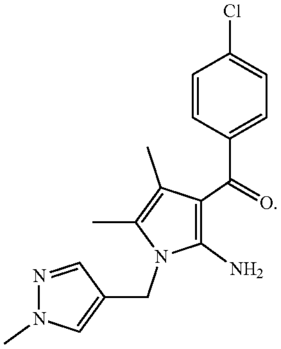
12. A compound represented by the following Chemical Formula 4 or a salt thereof:
[Chemical Formula 4]
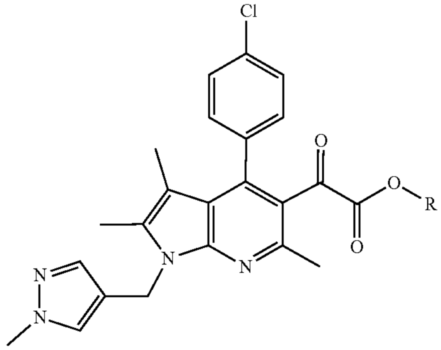
in the Chemical Formula above, R is $C_{1-4}$alkyl.
13. A compound represented by the following Chemical Formula 5 or a salt thereof:
[Chemical Formula 5]
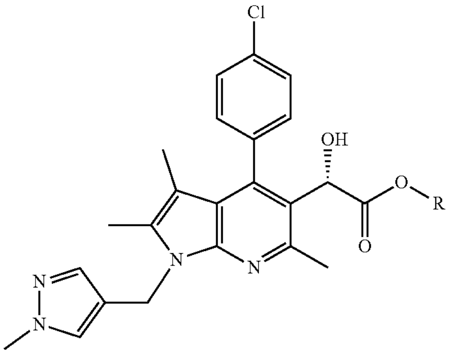
in the Chemical Formula above, R is $C_{1-4}$alkyl.
* * * * *